(12) United States Patent
Parmee

(10) Patent No.: US 11,320,562 B2
(45) Date of Patent: May 3, 2022

(54) RELATING TO DETECTORS

(71) Applicant: Cheyney Design & Development Ltd., Litlington (GB)

(72) Inventor: Richard Parmee, Litlington (GB)

(73) Assignee: Cheyney Design & Development Ltd.

( * ) Notice: Subject to any disclaimer, the term of this patent is extended or adjusted under 35 U.S.C. 154(b) by 134 days.

(21) Appl. No.: 16/616,117

(22) PCT Filed: May 23, 2018

(86) PCT No.: PCT/GB2018/051393
§ 371 (c)(1),
(2) Date: Nov. 22, 2019

(87) PCT Pub. No.: WO2018/215762
PCT Pub. Date: Nov. 29, 2018

(65) Prior Publication Data
US 2020/0174154 A1 Jun. 4, 2020

(30) Foreign Application Priority Data

May 23, 2017 (GB) .................................... 1708270

(51) Int. Cl.
*G01V 5/00* (2006.01)
*G01N 23/04* (2018.01)
(Continued)

(52) U.S. Cl.
CPC .......... *G01V 5/0041* (2013.01); *G01N 23/04* (2013.01); *G01N 33/12* (2013.01); *G06T 7/0004* (2013.01); *G06T 2207/30128* (2013.01)

(58) Field of Classification Search
CPC ...... G01V 5/0041; G01N 33/12; G01N 23/04; G06T 7/0004; G06T 2207/30128
See application file for complete search history.

(56) References Cited

U.S. PATENT DOCUMENTS 6,370,223 B1    4/2002  Gleason et al.
8,280,005 B2 *  10/2012  Suyama .................. G01N 23/04
                                                          378/98.9
(Continued)

FOREIGN PATENT DOCUMENTS

EP      3141186 A1    3/2017
JP   2008279153 A    11/2008
(Continued)

OTHER PUBLICATIONS

International Search Report and Written Opinion for International Application No. PCT/GB2018/051393, dated Dec. 11, 2018, 14 pages.
(Continued)

*Primary Examiner* — Brenda C Bernardi
(74) *Attorney, Agent, or Firm* — RatnerPrestia

(57) ABSTRACT

A method for optimising detector performance in a dual-energy detector system including high-energy X-ray detection and low-energy X-ray detection. The method includes one or more steps from a group including: utilising different scanning rates for high-energy X-ray detection and low-energy X-ray detection; utilising different integration times for high-energy Xray detection and low-energy X-ray detection; and/or utilising different diode sizes for high-energy X-ray detection and low-energy X-ray detection.

17 Claims, 2 Drawing Sheets

(51) Int. Cl.
*G01N 33/12* (2006.01)
*G06T 7/00* (2017.01)

(56) References Cited

U.S. PATENT DOCUMENTS

| | | | |
|---|---|---|---|
| 10,006,873 B1* | 6/2018 | Davis, III | G01N 23/04 |
| 2009/0147919 A1* | 6/2009 | Goto | A61B 6/482 |
| | | | 378/86 |
| 2010/0119038 A1* | 5/2010 | Suyama | G01V 5/0041 |
| | | | 378/57 |
| 2013/0039462 A1* | 2/2013 | Morton | G21K 1/02 |
| | | | 378/57 |
| 2017/0065240 A1* | 3/2017 | Zou | G01N 23/044 |
| 2018/0164231 A1* | 6/2018 | Davis, III | G01N 23/04 |
| 2018/0188191 A1* | 7/2018 | Davis, III | G01N 33/12 |
| 2019/0257773 A1* | 8/2019 | Murray | G01N 33/12 |
| 2020/0057008 A1* | 2/2020 | Suyama | G01N 23/18 |

FOREIGN PATENT DOCUMENTS

| | | | | |
|---|---|---|---|---|
| WO | 2012137205 A1 | 10/2012 | | |
| WO | WO-2017191563 A1 * | 11/2017 | | G01T 1/241 |

OTHER PUBLICATIONS

International Preliminary Report on Patentability for International Application No. PCT/GB2018/051393, dated Nov. 26, 2019, 9 pages.

* cited by examiner

RELATING TO DETECTORS

CROSS REFERENCE TO RELATED APPLICATIONS

This application is the U.S. National Stage filing of International Appln. No. PCT/GB2018/051393, filed May 23, 2018, which claims priority to GB Application No. 1708270.2, filed May 23, 2017, each of which being incorporated herein by reference for all purposes.

FIELD OF THE INVENTION

The present invention relates to detectors for food products. In particular, the present invention relates to: a method for optimising detector performance in a dual-energy detector system, an apparatus, for improving bone detection in poultry; and a method for improving foreign object detection in a food product.

BACKGROUND OF THE INVENTION

Scanning machines typically use X-ray detectors for scanning food products on production lines. The primary aim of such machines is to detect bone fragments, or other foreign objects, which should not be in the food product as supplied to a customer/consumer. It is known to use dual-energy X-ray detection for scanning food products. It is also known to use laser height measurement detection to determine a thickness of food products. The inspection of chicken fillets, tenders and other parts using X-rays has traditionally been a difficult application owing to the nature of avian bones and shape/artefacts of the food matrix. Some detection systems currently exist, but those being marketed exhibit limited detection, high false reject levels, and are expensive.

Laser height measurement is known to be used for detecting the thickness of a food product to be scanned, so as to enable it to be correlated with an associated X-ray image. Taking a chicken breast as an example of such a food product, occlusions typically occur around the periphery of the chicken breast or where, owing to the shape of the breast, a portion of the breast may overhang an underlying void, or region obscured from view. Laser height measurement cannot by itself accurately measure those regions and can only assume that the breast extends fully beneath the point of detection and that there is no form of overhang. When one considers that it is within the occlusions that there is a higher likelihood of there being bones, in particular the wishbone or fan bone, this draws attention to a significant limitation of systems incorporating laser height measurement in bone detection.

In present detector systems having more than one form of detection, it is important that images from the more than one detector are well synchronised, otherwise the combination of signals will be ineffective. Present systems are only capable of synchronising images from two or more detectors to an alignment of, approximately, +/− one pixel.

Accordingly, the present invention is aimed at providing an improved detector and associated methods.

SUMMARY OF THE INVENTION

According to a first aspect, the present invention provides a method for optimising detector performance in a dual-energy detector system comprising high-energy X-ray detection and low-energy X-ray detection, wherein the method comprises one or more steps from a group comprising:
utilising different scanning rates for high-energy X-ray detection and low-energy X-ray detection;
utilising different integration times for high-energy X-ray detection and low-energy X-ray detection; and/or
utilising different diode sizes for high-energy X-ray detection and low-energy X-ray detection.

Preferably, the method comprises over-scanning with high-energy X-ray scanning as compared to low-energy X-ray scanning. Preferably, high-energy X-ray scanning is at about 2 to about 32 times faster than low-energy X-ray scanning, or high-energy X-ray scanning at about 2 to about 16 times faster than low-energy X-ray scanning, or at about 2 to about 8 times faster. Most preferably, high-energy X-ray scanning is at least about 4 times faster. As such, high-energy scanning is over-scanned, which assists in achieving improved synchronisation.

Preferably, utilising different integration times from about 5 milliseconds (ms) to about 200 microseconds (µs), or utilising different integration times from about 5 milliseconds to about 1 millisecond.

Preferably, the method comprises combining the image created by high-energy X-ray detection with the image created by low-energy X-ray detection, so as to substantially precisely synchronise the images.

Preferably, image synchronisation is provided within +/−0.25 of a pixel or within as little as $\frac{1}{8}$, $\frac{1}{16}$ or $\frac{1}{32}$ of a pixel.

Preferably, improving synchronisation by utilising smaller diode sizes for high-energy X-ray detection, so as to compensate for the difference in photon flux at the different energy levels of high- and low-energy X-ray detectors.

Preferably, a high-energy X-ray detector operates at about 2 to about 5 times the kV of a low-energy X-ray detector. Most preferably, the high-energy X-ray detector operates at, at least, 2 times the kV of the low-energy X-ray detector.

Preferably, the photon flux of a/the high-energy detector will be about 2 to about 32 times that of a/the low-energy detector.

A method for optimising detector performance in a dual-energy detector system, substantially as herein disclosed, with reference to the accompanying description and/or any example described herein.

Preferably, high-energy X-ray detection and low-energy X-ray detection are conducted in substantially the same plane of detection. Preferably, high-energy X-ray detection and low-energy X-ray detection are coplanar. Most preferably, high-energy X-ray detection and low-energy X-ray detection are sequential.

Preferably, high-energy X-ray detection and low-energy X-ray detection are conducted substantially in parallel planes.

Preferably, the method comprises aligning the focal point(s) of high-energy X-ray detection and low-energy X-ray detection.

Preferably, aligning the focal points at a distance 'y1' from a conveyor bed or object plane of the apparatus.

Preferably, aligning the focal points at a distance 'y2' from an approximate top of said item to be scanned.

Preferably, the method further comprises creating a 'pseudo X-ray' image of an item to be scanned using laser height measurement means and comparing the 'pseudo X-ray' image and at least one X-ray image, so as to improve foreign object detection.

Preferably, the method further comprises comparing the 'pseudo X-ray' image with an image created by high-energy X-ray detection and an image created by low-energy X-ray detection.

Preferably, creating a 'pseudo X-ray' image from data supplied by the laser height measurement means and one or more known or predicted properties of said item to be scanned.

Preferably, conducting X-ray detection and laser detection in a coplanar manner and/or aligning the focal point(s) of X-ray detection and laser detection. Most preferably, X-ray detection and laser detection are sequential.

Preferably, the method further comprises zoning a food product so as to determine preferred data usage options selected from:
laser height measurement data and low-energy X-ray data; or
dual-energy X-ray data; or laser height measurement data and dual-energy X-ray data.

Most preferably, the zoning comprises utilising:
laser height measurement means to determine a height profile of various parts of the food product, and selecting one or more zones for preferred data combinations;
geometrical position data within about 30 mm, about 20 mm or about 10 mm of a periphery of the food product; and/or
X-ray greyscale data, as an alternative way of defining height.

Most preferably, zoning comprises identifying one or more edge regions of the food product and one or more central regions.

According to a second aspect, the present invention provides a dual-energy detector system comprising high-energy X-ray detection and low-energy X-ray detection, wherein the apparatus comprises any one or more of the group comprising:
means for utilising different scanning rates for high-energy X-ray detection and low-energy X-ray detection;
means for utilising different integration times for high-energy X-ray detection and low-energy X-ray detection; and/or
means for utilising different diode sizes for high-energy X-ray detection and low-energy X-ray detection.

Preferably, a high-energy X-ray detector, a low-energy X-ray detector and a laser detector are mounted so as to be coplanar.

Preferably, the apparatus is arranged such that high-energy X-ray detection and low-energy X-ray detection are conducted in substantially the same plane of detection. Most preferably, high-energy X-ray detection and low-energy X-ray detection are sequential.

Preferably, the apparatus is arranged such that for high-energy X-ray detection and low-energy X-ray detection is conducted substantially in parallel.

Preferably, the apparatus is arranged such that a focal point of high-energy X-ray detection aligns with a focal point of low-energy X-ray detection X-ray imaging means. Most preferably, the focal points are aligned along a notional isohypse.

Preferably, the apparatus further comprises means for zoning of an item to be scanned so as to determine preferred data usage options selected from:
laser height measurement data and low-energy X-ray data; or
dual-energy X-ray data; or
laser height measurement data and dual-energy X-ray data.

Preferably, the means for zoning utilises:
laser height measurement means to determine a height profile of various parts of the food product, and selecting one or more zones for preferred data combinations;
geometrical position data within about 30 mm, about 20 mm or about 10 mm of a periphery of the food product; and/or
X-ray greyscale data, as an alternative way of defining height.

Preferably, the means for zoning identifies one or more edge regions of said item to be scanned and one or more central regions.

Preferably, the apparatus further comprises laser height measurement means for creating a 'pseudo X-ray' image of an/the item to be scanned and means for comparing the 'pseudo X-ray' image and at least one X-ray image to improve foreign object detection. Most preferably, X-ray detection and laser detection are sequential.

According to a third aspect, the present invention provides an apparatus, for improving bone detection in poultry, the apparatus comprising:
laser height measurement means, for creating a 'pseudo X-ray' image of an item to be scanned;
X-ray imaging means, for creating an X-ray image of said item; and
means for comparing the 'pseudo X-ray' image and the X-ray image, so as to improve foreign object detection in said item.

The 'pseudo X-ray' image is a predicted X-ray image, specifically not created by X-ray imaging.

Preferably, the laser height measurement means comprises means for creating a 'pseudo X-ray' image from data supplied by the laser height measurement means and one or more known or predicted properties of said item to be scanned.

Preferably, the one or more known properties relate to a type of foodstuff being scanned, for example a known density of such foodstuffs or radiographic opacity.

Preferably, the means for creating [the 'pseudo X-ray image'] is arranged to create an image without the effect of foreign objects.

Preferably, the apparatus is arranged such that laser detection and X-ray detection are conducted in substantially the same plane of detection.

Preferably, the apparatus is arranged such that laser detection and X-ray detection is conducted substantially in parallel.

Preferably, the apparatus is arranged such that a focal point of the laser height measurement means aligns with a focal point of the X-ray imaging means. Most preferably, the focal points are aligned along a notional isohypse.

Preferably, the focal points are aligned at a distanc 'y1' from a conveyor bed or object plane of the apparatus.

Preferably, the focal points are aligned at a distance 'y2' from an approximate top of said item to be scanned.

Preferably, the apparatus further comprises an X-ray imaging means, such that a dual-energy X-ray apparatus is provided, one of high-energy and one of low-energy.

Preferably, the apparatus comprises means for zoning said item to be scanned so as to determine preferred data usage options selected from:
laser height measurement data and low-energy X-ray data; or dual-energy X-ray data; or
laser height measurement data and dual-energy X-ray data.

Preferably, the means for zoning utilises data from the laser height measurement means to determine a height profile of various parts of said item to be scanned, and selects one or more zones for preferred data combinations. Alternatively, zoning could be based upon geometrical position, for example, within about 30 mm, about 20 mm or about 10 mm of a periphery of said item to be scanned, or using X-ray greyscale, which would provide an alternative way of defining height.

Preferably, the means for zoning identifies one or more edge regions of said item to be scanned and one or more central regions.

An apparatus, for improving bone detection in poultry, substantially as herein disclosed, with reference to FIG. 1, 2 or 3 of the accompanying drawings and/or any example described herein.

According to a fourth aspect, the present invention provides a method for improving foreign object detection in a food product, the method comprising:

scanning the food product with laser height measurement means and creating
a 'pseudo X-ray' image of the food product;
scanning the food product with X-ray imaging means and creating an X-ray image of the food product; and
comparing the 'pseudo X-ray' image and the X-ray image to improve detection of foreign objects in the food product.

Preferably, detection is conducted substantially in the same plane.

Preferably, detection is conducted substantially in parallel, such as by aligning the laser height measurement means and the X-ray imaging means in parallel.

Preferably, a focal point of the laser height measurement means is aligned with a focal point of the X-ray imaging means. Most preferably, X-ray detection and laser detection are sequential.

Preferably, the focal points are aligned at a distance 'y1' from a conveyor bed or object plane of a scanning apparatus.

Preferably, the focal points are aligned at a distance 'y2' from an approximate top of the food product.

Preferably, scanning the food product with a further X-ray imaging means to provide dual-energy X-ray scanning, one of high-energy and one of low-energy.

Preferably, zoning the food product so as to determine preferred data usage options selected from:

laser height measurement data and low-energy X-ray data; or dual-energy X-ray data; or
laser height measurement data and dual-energy X-ray data.

Preferably, utilising laser height measurement means to determine a height profile of various parts of the food product, and selecting one or more zones for preferred data combinations. Alternatively, zoning could be based upon geometrical position, for example, within about 30 mm, about 20 mm or about 10 mm of a periphery of said item to be scanned, or using X-ray greyscale, which would provide an alternative way of defining height.

Preferably, identifying one or more edge regions of the food product and one or more central regions.

Preferably, the method further comprises a method for optimising detector performance in a dual-energy detector system, according to any one or more features of the first aspect.

A method for improving foreign object detection in a food product, substantially as herein disclosed, with reference to the accompanying description and/or any example described herein.

The present invention also relates to a data carrier, disk, chip, computer, tablet or the like programmed to implement the method of any one or more features of the second aspect or the third aspect, or a piece of software stored on any such device coded to implement the method of any one or more features of the second aspect or the third aspect.

Advantageously, aligning the geometries of detectors, whether X-ray or laser, to be coplanar and/or aligning the focal points of detectors makes image correlation easier and improves detection.

Advantageously, the focal point of the laser is aligned with the focal point(s) of the X-ray generator(s) at the same height (isophypse)/distance from the food product. In this way, the beam path of the laser device through the object would match the corresponding beam path(s) of the X-rays. If using a dual-energy X-ray system, then the focal point(s) of both X-ray generator(s) are at the same height (isophypse)/distance from the food product.

Advantageously, correlation of images is both easier and improved, as the focus of the X-ray detection and the laser detection is the same, and the path length for X-ray detection and laser detection is the same. If using a dual-energy X-ray system, then the focus of the X-ray detection is the same for each, and the path length of the X-ray detection is the same for each.

Zoning is advantageous because the occluded regions are generally at the very edge of the food product, in particular the chicken fillet, where there is likely to be occurrence of bones, such as the wishbone. In particular, laser detection provides better accuracy for an assessment of the centre of the fillet where the meat is at its thickest, which is also the region where dual-energy detection is at its least effective.

With respect to a dual-energy X-ray system, the effects of having different scanning rates is that: one can match the two detector outputs more accurately, which will optimise the use of the respective dynamic ranges; one can combine multiple rows of the high-energy detector, thereby improving the signal to noise ratio; and one can achieve more accurate synchronisation between low- and high-energy images. The effects of having different integration times, irrespective of the scanning interval, provides a matching output that will optimise the dynamic ranges and signal to noise ratios of the detectors.

BRIEF DESCRIPTION OF THE DRAWING FIGURES

The invention will now be disclosed, by way of example only, with reference to the following drawings, in which.

DETAILED DESCRIPTION OF THE INVENTION

Figure 1:
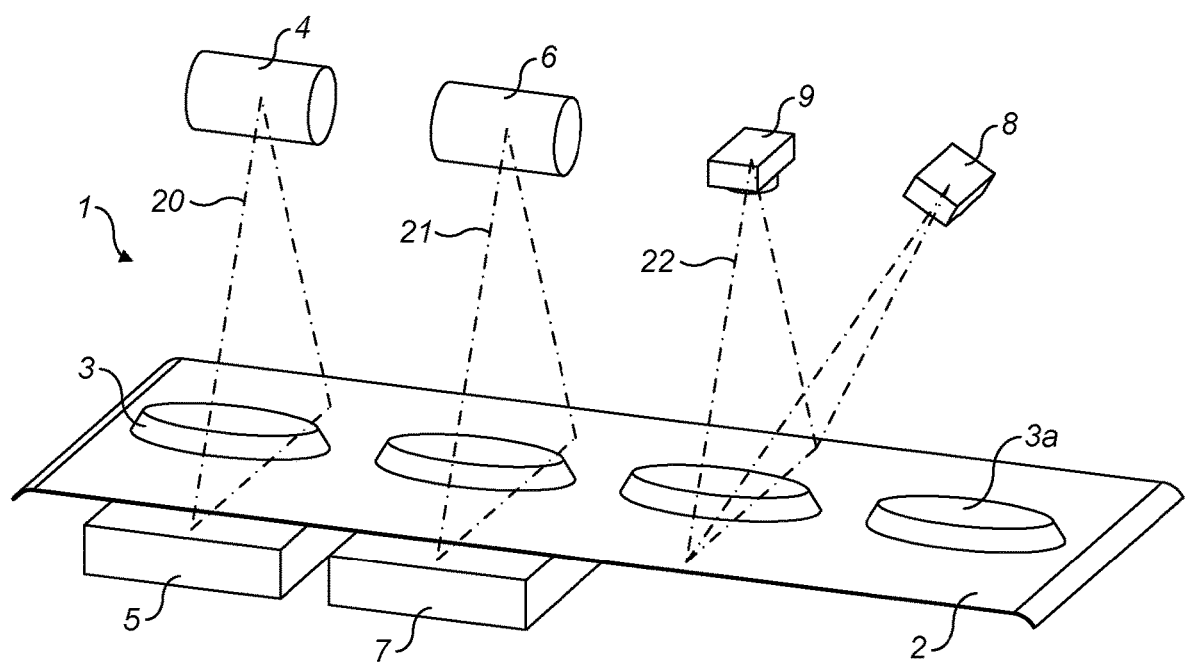
FIG. 1 is a schematic perspective view of a dual-energy X-ray and laser detector apparatus.

FIG. 1 shows a dual-energy X-ray and laser detector apparatus, generally identified by reference 1. The apparatus 1 includes a conveyor 2 of a production line for supplying a plurality of food products 3 to be tested by the apparatus 1. The apparatus 1 further includes two X-ray detectors, in the form of a high-energy X-ray generator 4 and associated high-energy X-ray detector 5, and a low-energy X-ray generator 6 and associated low-energy X-ray detector 7. The apparatus further includes a laser height measurement detector, in the form of a laser source 8 and a laser profilometer 9. Both X-ray generators 4; 6 and the laser profilometer 9 are mounted above the conveyor 2 in a coplanar relationship—the laser source 8 is also mounted above the conveyor 2 (mountings not shown), such that sequential detection in provided as a food product 3 moves along the conveyor 2.

In an alternative to what is shown in FIG. 1, the apparatus may be provided by a single X-ray detector, being an X-ray generator and associated detector, in combination with a laser height measurement detector. As a further alternative, the apparatus may be provided by dual-energy X-ray detectors, in the form of a high-energy X-ray generator and associated high-energy X-ray detector and a low-energy X-ray generator and associated low-energy X-ray detector, without a laser height measurement detector.

General operation of X-ray detectors is known in the art and X-rays are passed through the food product 3 and are detected beneath the conveyor 2. General operation of the laser height measurement detector is also known in the art. Accordingly, neither require a detailed explanation. However, the present invention provides a number of differences to the set-up and operation of those detectors, which will now be further explained.

Figure 2:
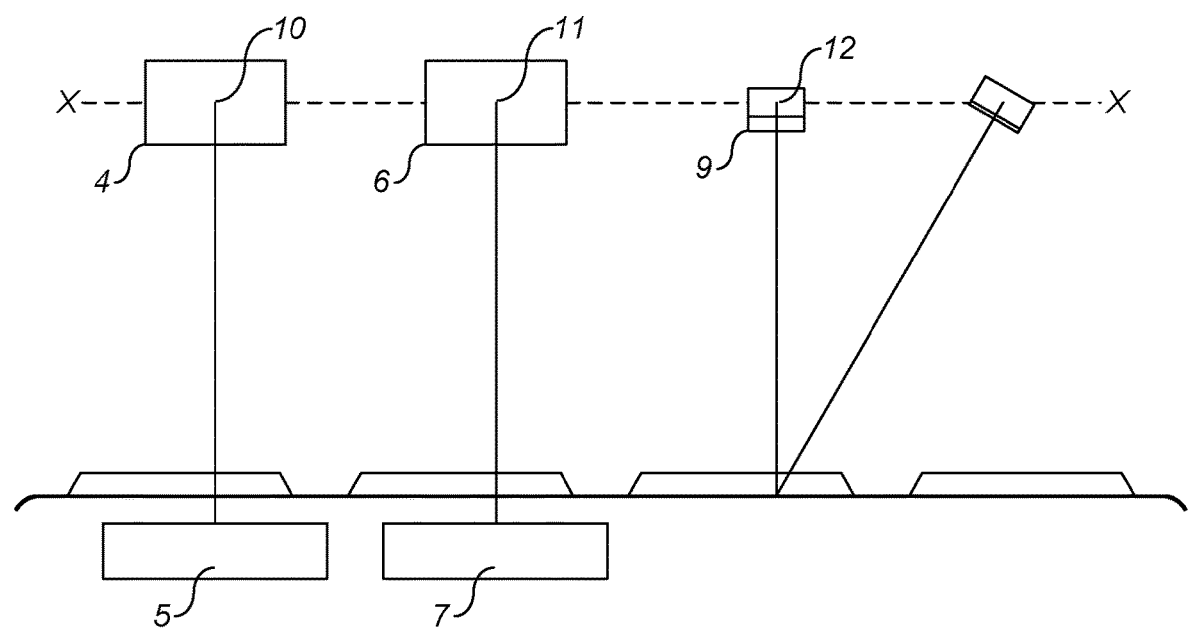
FIG. 2 is a schematic side-view of the detector apparatus of FIG. 1.
Figure 3:
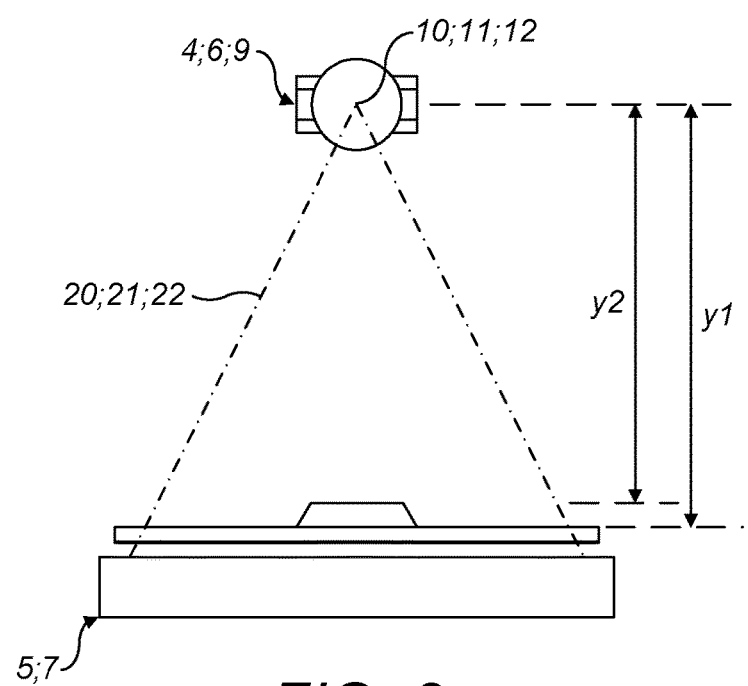
FIG. 3 is a schematic end-view of the detector apparatus of FIG. 1.

The approximate geometries of detection are shown in FIGS. 1 and 2, in particular. The geometry of high-energy X-ray detection is indicated by the region bounded by the dash-dot line having reference 20, the geometry of low-energy X-ray detection is identified by the region bounded by the dash-dot line having reference 21 and the geometry of laser height measurement detection is identified by the region bounded by the dash-dot line having reference 22. As can be noted from those Figures, the geometries of detection 20; 21; 22 are substantially aligned in the sense that the detectors are provided in-line such that a food product 3 passes individually through all detectors in a linear manner and in the sense that those geometries of detection 20; 21; 22 are approximately parallel to each other. In addition, focal points 10; 11 of the X-ray generators 4; 6 and a focal point 12 of the laser profilometer 9 are aligned as shown by line X-X in FIG. 2, and provided at the same path length or distance 'y2' from the food product 3—and path length or distance 'y1' from the conveyor 2. The distances 'y2' and 'y1', where y1>y2, may be from about 300 mm to about 700 mm. FIG. 3, an end-view looking along the conveyor 2, shows alignment of the X-ray generators 4; 6 and the laser profilometer 9, and shows the respective distances 'y2' and 'y1', which are common for all of the detectors. This arrangement of geometries of detection 20; 21; 22 and alignment of focal points 10; 11; 12 makes correlation between images easier to calculate. Accordingly, detection of foreign objects in the food product 3 is improved.

The apparatus includes a system (not shown) having a processor and associated memory for capturing data from the detectors, analysing such data, and providing output images.

In use, laser height measurement allows one to create a 'pseudo X-ray' image—i.e. an image calculated to show what an X-ray image of the food product 3 being tested would look like if it were pure muscle, with no bone. Such a 'pseudo X-ray' image provides a good reference image against which to compare the true X-ray image or images—which image(s) may include bone. Of course, if the data from only one X-ray scan is utilised, the 'pseudo X-ray' image is compared to a single true X-ray image, whereas, in the alternative, if the data from both X-ray scans is utilised, the 'pseudo X-ray' image is compared to both true X-ray images. Comparing the 'pseudo X-ray' and X-ray image(s) is, essentially a process of subtracting the 'pseudo X-ray' image from the real X-ray image(s). If no bone is detected in the food product, there would be practically no difference in the images and a resulting image would be substantially black. However, if a bone is detected in the X-ray image(s), then a difference would be provided in a resulting image such that the bone would be identified by a white-ish region. Such a food product could then be diverted from the main production line for disposal or further review and rework.

Using chicken breasts as an example, it is often in the occluded regions that any bones will be located, for example, parts of the wishbone may be found in edge regions of the breast. Accordingly, the food product may be zoned so as to identify one or more edge regions in which occlusions may be expected and one or more central regions in which no occlusions are expected. In one example, zoning involves use of laser height measurement data in the system so as to select the one or more edge regions and the one or more central regions. Once zoned, the system determines the best combination of detector data for detecting bones in the one or more edge regions and one or more central regions, and then conducts further analysis. As such, in (typically) edge regions, where laser detection is occluded, the system uses dual-energy detection data. Whereas, in the (typically) central regions, where laser detection is not occluded, the system uses a combination of laser detection data and low-energy X-ray detection data. By way of alternatives, zoning could be achieved through analysis of geometrical data or X-ray detector data. Accordingly, the combinations of detector data described above provide optimum detection at the edges and centre of food products to be scanned.

Those skilled in the art will understand that aligning the geometries of detectors, whether X-ray or laser, to be coplanar and/or aligning the focal points of detectors makes image correlation easier and improves detection.

With respect to optimising detector performance in a dual-energy detector system comprising high-energy X-ray detection and low-energy X-ray detection, which can be also in combination with laser height measurement detection, energy discrimination in the two independent X-ray detectors (4; 5 and 6; 7) is achieved by means of, for high-energy, use of a selected scintillator and metal filter, and, for low-energy, use of a selected scintillator or direct conversion.

The high-energy X-ray generator 4 will operate at, at least, two times the kV of the low-energy generator 6, which will then provide an output photon flux of, at least, four times that of the low-energy generator 6. The high-energy detector (4; 5) will scan the food product 3 faster than the low-energy detector (6; 7) at, at least, four times the rate. This allows the system to combine the data from multiple rows of the high-energy detector (4; 5) in such a combination as to relatively precisely synchronise the image with the low-energy detector image to within +/−0.25 of a pixel. The effects of such an arrangement are that: one can match the two detector outputs more accurately, which will optimise the use of the respective dynamic ranges; one can combine multiple rows of the high-energy X-ray detector, thereby improving the signal to noise ratio; and one can achieve more accurate synchronisation between the low- and high-energy X-ray images.

As an alternative to the above, or in addition, the two X-ray detectors may operate with different integration times, irrespective of the scanning interval, so as to provide a matching output that will optimise the dynamic ranges of the detectors.

In addition to either varying scanning rates and/or integration times of the two X-ray detectors, a smaller diode size may be used in the array of the high-energy detector 5, so as to help compensate for the difference in photon flux at the different energy levels of the high-energy and low-energy detectors (4; 5 and 6; 7). A combination of this with faster scanning rates for high-energy X-ray detection (i.e. overscanning) will result in improved detection of metallic foreign bodies in the product. Although it is not wished to be bound by theory, it is well-known that higher-energy detection can result in improved detection of high-atomic number contaminants.

Other methods for optimising detector performance may be to alter the scintillator and/or metal filter.

Those skilled in the art will understand that such improved dual-energy X-ray detection may be conducted alone, or in combination with laser height measurement.

The invention claimed is:

1. A method for optimising detector performance in a dual-energy detector system comprising sequential high-energy X-ray detection and sequential low-energy X-ray detection of a food product moving along a conveyor of a production line, wherein the method comprises:
   (a) (i) utilising different scanning rates for high-energy X-ray detection and low-energy X-ray detection; (ii) utilising different integration times for high-energy X-ray detection and low-energy X-ray detection; and/or (iii) utilising different diode sizes for high-energy X-ray detection and low-energy X-ray detection; and
   (b) combining an image of the food product created by high-energy X-ray detection with an image of the food product created by low-energy X-ray detection, so as to synchronize alignment of the images.

2. The method as claimed in claim 1 comprising either high-energy X-ray scanning at about 2 to about 32 times faster than low-energy X-ray scanning, or high-energy X-ray scanning at about 2 to about 8 times faster than low-energy X-ray scanning.

3. The method as claimed in claim 1 comprising either utilising different integration times from about 5 milliseconds (ms) to about 200 microseconds (μs), or utilising different integration times from about 5 milliseconds to about 1 millisecond.

4. The method as claimed in claim 1 comprising improving synchronisation by utilising smaller diode sizes for high-energy X-ray detection, so as to compensate for a difference in photon flux at the different energy levels of high- and low-energy X-ray detectors.

5. The method as claimed in claim 1, wherein high-energy X-ray detection and low-energy X-ray detection are conducted in, either
   (i) substantially the same plane of detection, or
   (ii) substantially parallel planes.

6. The method as claimed in claim 1 comprising aligning focal point(s) of high-energy X-ray detection and low-energy X-ray detection.

7. The method as claimed in claim 6 comprising aligning the focal points at, either
   (i) a distance y1 from a conveyor bed or object plane of an apparatus, or
   (ii) a distance y2 from an approximate top of an item to be scanned.

8. The method as claimed in claim 1 further comprising creating a pseudo X-ray image of an item to be scanned using laser height measurement means or laser height measurement means and one or more known or predicted properties of said item to be scanned, and comparing the pseudo X-ray image and at least one X-ray image, so as to improve foreign object detection.

9. The method as claimed in claim 8 comprising comparing the pseudo X-ray with an image created by high-energy X-ray detection and an image created by low-energy X-ray detection.

10. The method as claimed in claim 8 comprising:
    (i) conducting X-ray detection and laser detection in a coplanar manner, and/or
    (ii) aligning the focal point(s) of X-ray detection and laser detection.

11. The method as claimed in claim 1 comprising zoning a food product by:
    (i) utilising laser height measurement means to determine a height profile of various parts of the food product, and selecting one or more zones for preferred data combinations;
    (ii) utilising geometrical position data within about 30 mm, about 20 mm or about 10 mm of a periphery of the food product;
    (iii) utilising X-ray greyscale data, as an alternative way of defining height, and/or
    (iv) identifying one or more edge regions of the food product and one or more central regions, so as to determine preferred data usage options selected from: laser height measurement data and low-energy X-ray data; dual-energy X-ray data; or laser height measurement data and dual-energy X-ray data.

12. A dual-energy detector system configured for detection of a food production moving along a conveyor, the dual-energy detector system comprising:
    (a) sequential high-energy X-ray detector and sequential low-energy X-ray detector;
    (b) (i) means for utilising different scanning rates for the high-energy X-ray detector and the low-energy X-ray detector; (ii) means for utilising different integration times for the high-energy X-ray detector and the low-energy X-ray detector; and/or (iii) means for utilising different diode sizes for the high-energy X-ray detector and the low-energy X-ray; and
    (c) means for combining an image created by the high-energy X-ray detector with an image created by the low-energy X-ray detector, so as to synchronize alignment of the images.

13. The detector system as claimed in claim 12 further comprising laser height measurement means for creating a pseudo X-ray image of an item to be scanned and means for comparing the pseudo X-ray image and at least one X-ray image to improve foreign object detection.

14. The detector system as claimed in claim 12 wherein the high-energy X-ray detector, the low-energy X-ray detector and/or a laser height measuring means are mounted so as to be coplanar, in use.

15. The detector system as claimed in claim 12 wherein the system further comprises:
    (d) (i) laser height measurement means to determine a height profile of various parts of the food product, and selecting one or more zones for preferred data combinations; (ii) geometrical position data within about 30 mm, about 20 mm or about 10 mm of a periphery of the food product; (iii) X-ray greyscale data, as an alternative way of defining height, and/or (iv) means for identifying one or more edge regions of the food product and one or more central regions, so as to determine preferred data usage options selected from: laser height measurement data and low-energy X-ray data; dual-energy X-ray data; or laser height measurement data and dual-energy X-ray data.

16. A method for optimising detector performance in a dual-energy detector system comprising high-energy X-ray detection and low-energy X-ray detection, wherein the method comprises:
  (a) (i) utilising different scanning rates for high-energy X-ray detection and low-energy X-ray detection; (ii) utilising different integration times for high-energy X-ray detection and low-energy X-ray detection; and/or (iii) utilising different diode sizes for high-energy X-ray detection and low-energy X-ray detection, and
  (b) (i) utilising laser height measurement means to determine a height profile of various parts of the food product, and selecting one or more zones for preferred data combinations; (ii) utilising geometrical position data within about 30 mm, about 20 mm or about 10 mm of a periphery of the food product; (iii) utilising X-ray greyscale data, as an alternative way of defining height, and/or (iv) identifying one or more edge regions of the food product and one or more central regions, so as to determine preferred data usage options selected from: laser height measurement data and low-energy X-ray data; dual-energy X-ray data; or laser height measurement data and dual-energy X-ray data.

17. The detector system as claimed in claim 12 wherein the high-energy X-ray detector, the low-energy X-ray detector and/or a laser height measuring means are mounted in-line, such that the food product passes individually through the detectors and/or the laser height measuring means in a linear manner.

* * * * *